US009370599B2

(12) United States Patent
Deane et al.

(10) Patent No.: US 9,370,599 B2
(45) Date of Patent: Jun. 21, 2016

(54) COIL ASSEMBLY FOR PLASMA GENERATION

(71) Applicant: Novaerus Patents Limited, County Dublin (IE)

(72) Inventors: Graham Deane, Dublin (IE); Kevin Maughan, Dublin (IE); Felipe Soberon, Dublin (IE)

(73) Assignee: Novaerus Patents Limited, Dublin (IE)

( * ) Notice: Subject to any disclaimer, the term of this patent is extended or adjusted under 35 U.S.C. 154(b) by 0 days.

(21) Appl. No.: 14/805,690

(22) Filed: Jul. 22, 2015

(65) Prior Publication Data
US 2015/0351212 A1    Dec. 3, 2015

Related U.S. Application Data

(63) Continuation of application No. 14/678,030, filed on Apr. 3, 2015.

(60) Provisional application No. 61/974,462, filed on Apr. 3, 2014.

(51) Int. Cl.
| *H05H 1/24* | (2006.01) |
| *A61L 9/16* | (2006.01) |
| *A61L 2/00* | (2006.01) |
| *A61L 9/00* | (2006.01) |

(52) U.S. Cl.
CPC ... *A61L 9/16* (2013.01); *A61L 2/00* (2013.01); *A61L 9/00* (2013.01); *H05H 1/2406* (2013.01); *H05H 2001/2418* (2013.01); *H05H 2001/2431* (2013.01)

(58) Field of Classification Search
CPC .................. A61L 9/16; H05H 1/2406; H05H 2001/2431; H05H 2001/2418
See application file for complete search history.

(56) References Cited

U.S. PATENT DOCUMENTS

| 6,893,618 | B2 | 5/2005 | Kotlyar |
| 7,192,553 | B2 | 3/2007 | Crowe |
| 7,279,028 | B2 | 10/2007 | Bergeron |
| 7,449,053 | B2 | 11/2008 | Hallam |
| 7,452,410 | B2 | 11/2008 | Begreron |
| 7,559,976 | B2 | 7/2009 | Krigmont |
| 8,361,402 | B2 | 1/2013 | Tsui |
| 8,673,068 | B2 | 3/2014 | Volodin |
| 2003/0007910 | A1 | 1/2003 | Diamant Lazarovich et al. |
| 2003/0132100 | A1 | 7/2003 | Crowe |
| 2004/0033176 | A1 | 2/2004 | Lee |

(Continued)

FOREIGN PATENT DOCUMENTS

| EP | 1285698 | 2/2003 |
| EP | 1433515 | 6/2004 |
| EP | 1666152 | 6/2006 |
| EP | 1715553 | 10/2006 |
| EP | 2085582 | 8/2009 |

(Continued)

*Primary Examiner* — Joseph L Williams
(74) *Attorney, Agent, or Firm* — Stephen T. Scherrer; Monique A. Morneault; Scherrer Patent & Trademark Law, P.C.

(57) ABSTRACT

A coil assembly for generating plasma, is disclosed. The coil assembly includes a cylindrical coil having a cylindrical inner mesh, a cylindrical outer mesh and a cylindrical dielectric separating the inner and outer meshes, an insulating stand at each of the first and second end of the cylindrical coil configured for mounting the cylindrical coil in an elevated position, wherein supply of voltage to the inner and outer meshes generates plasma which is discharged from the outer mesh.

16 Claims, 6 Drawing Sheets

(56) References Cited

U.S. PATENT DOCUMENTS

| | | |
|---|---|---|
| 2004/0052700 A1 | 3/2004 | Kotlyar |
| 2004/0184972 A1 | 9/2004 | Kelly |
| 2007/0020159 A1 | 1/2007 | Tsui |
| 2008/0283411 A1 | 11/2008 | Eastman |
| 2009/0274592 A1 | 11/2009 | Bergeron |
| 2010/0072055 A1 | 3/2010 | Tanaka |
| 2010/0168499 A1 | 7/2010 | Gutsol |

FOREIGN PATENT DOCUMENTS

| | | |
|---|---|---|
| EP | 2581925 | 4/2013 |
| GB | 2468865 | 9/2010 |
| GB | 2496888 | 5/2013 |
| JP | 2002143634 | 5/2002 |
| JP | 2012170869 | 9/2012 |
| WO | 2004047877 | 6/2004 |
| WO | 2008062554 | 5/2008 |
| WO | 2011149188 | 12/2011 |
| WO | 2013065205 | 5/2013 |

COIL ASSEMBLY FOR PLASMA GENERATION

TECHNICAL FIELD

The present invention relates to an air treatment method and apparatus. More specifically, the invention relates to a coil assembly that can be used to generate plasma for inactivating pathogens present in indoor air and removing pollutants from the same.

BACKGROUND OF THE INVENTION

Health threatening airborne pollutants may be subdivided into three groups; (a) airborne pathogens comprising any organism that causes disease that spreads throughout the environment via the air; (b) airborne allergens comprising any substance that, when ingested, inhaled, or touched, causes an allergic reaction and, (c) airborne volatile organic compounds (VOC) comprising any product that is designed to be sprayed at high pressure in the form of tiny particles that remain suspended in the air. The last category includes many cleaning chemicals, hair spray, various types of primer, and fuels such as gasoline and kerosene, as well as other household, beauty, or hobby products. Some fabrics, particularly those recently manufactured, also contribute to indoor airborne VOCs when they outgas, or leak out chemicals in gaseous form, over time.

Airborne pollutants can build up significantly in indoor environments with the result that the air that we breathe may become contaminated. Considering that on average humans spend approximately 90% of their time in an indoor environment, it will be appreciated that the removal of pollutants from indoor air is of importance to reduce allergies and prevent infection transmission, such as sick building syndrome.

Existing state of the art technologies for the control of airborne pathogens can be categorized as: (a) airborne trapping systems or filters, (b) airborne inactivation systems and, (c) some combination of the above.

Existing airborne inactivation technologies also include those that make use of chemicals, UV radiation and plasma discharge by-products.

Examples of chemical inactivation include the use of antimicrobial vaporizers, typically ozone or hydrogen peroxide. While these systems are effective, they are also disruptive, requiring the evacuation of indoor space to be treated and therefore are not suitable for use under normal living circumstances.

Alternative inventions for the purification of air comprise the use of ultra violet light (UV) emission to kill airborne bacteria. For example, international publication No. WO 2003/092751, describes a device in which a fluid (e.g. air) is passed through an array of UV lamps. It is appreciated that in this solution the one and only inactivation mechanism is via UV radiation.

Prior art also includes the use of plasma radicals for sterilisation of air filter medium; see for example US patent publication No. 2004/0184972 A1. In this prior art document, it is proposed that an upstream plasma discharge can generate active radicals which flow upstream to a medium filter and kill any bacteria or virus trapped by the filter.

In such systems which rely on plasma discharge, the design and configuration of the plasma generator are of particular importance. The teachings disclosed in the present document offers a viable coil assembly for plasma generation which can be used for air disinfection and pollution control.

SUMMARY

The present disclosure relates to a coil assembly that can be used to generate plasma for inactivating pathogens present in indoor air and removing pollutants from the same coil assembly for generating plasma.

In an embodiment of the present disclosure, a coil assembly for generating plasma comprises a cylindrical coil having a cylindrical inner mesh, a cylindrical outer mesh and a cylindrical dielectric separating the inner and outer meshes, an insulating stand at each of the first and second end of the cylindrical coil configured for mounting the cylindrical coil in an elevated position, wherein supply of voltage to the inner and outer meshes generates plasma which is discharged from the outer mesh.

Additional features and advantages of the present disclosure are described in, and will be apparent from, the detailed description of the presently preferred embodiments and from the drawings.

BRIEF DESCRIPTION OF THE DRAWINGS

The present application will now be described with reference to the accompanying drawings in which.

DETAILED DESCRIPTION

The present teachings relate to a coil assembly that generates a plasma discharge field to effectively sterilise air of micro-organisms or pathogens or oxidise organic airborne contaminants and particles.

Figure 1:
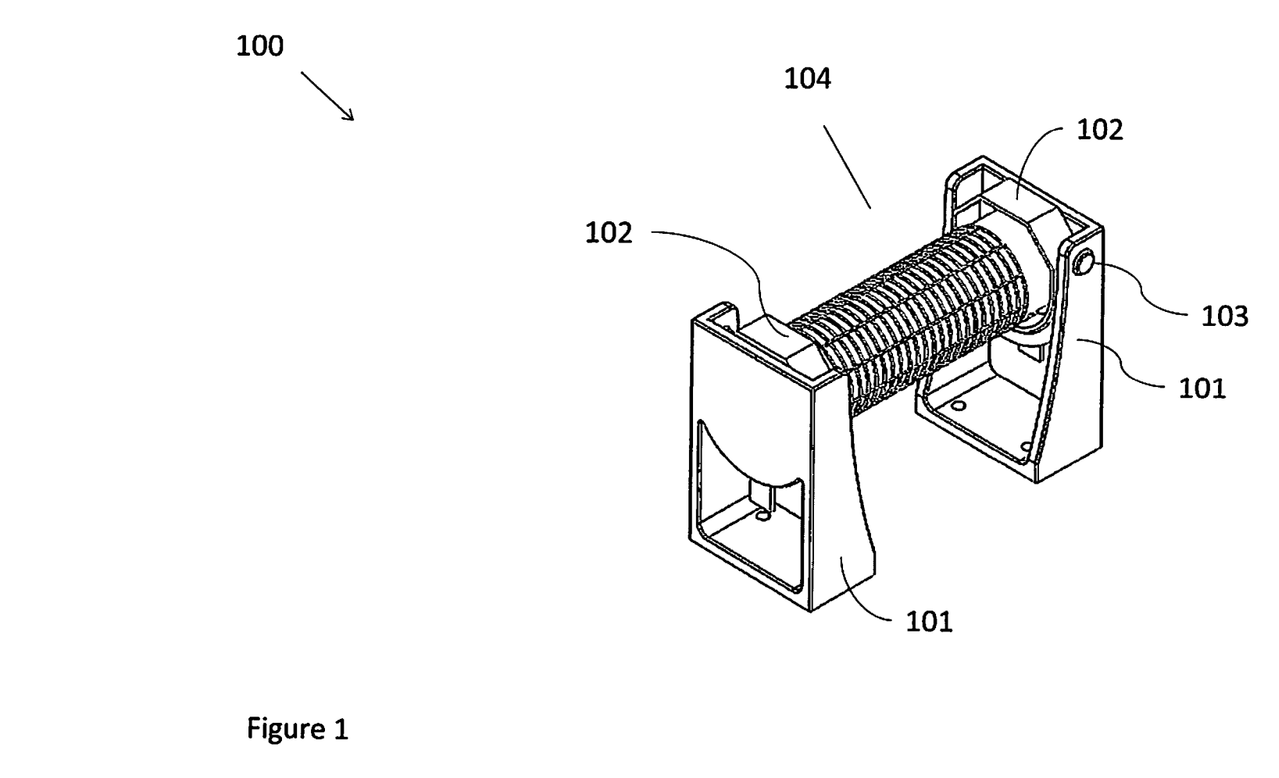
FIG. 1 is a perspective view of the coil assembly of the present invention.

The configuration of the coil assembly 100 is best described with reference to FIG. 1, which shows a cylindrical coil 104 held by insulated stands 101. Dielectric retainers 103 are used to secure the cylindrical coil 104 in place. Dielectric insulator caps 102 are provided at each end of the cylindrical coil to further insulate the cylindrical coil 104 from the insulated stands 101. This also ensures that the cylindrical coil is insulated from any surface that the stands 101 may be mounted upon. The insulator caps 102 have a further function in that they hold the cylindrical coil 104 together.

Figure 2:
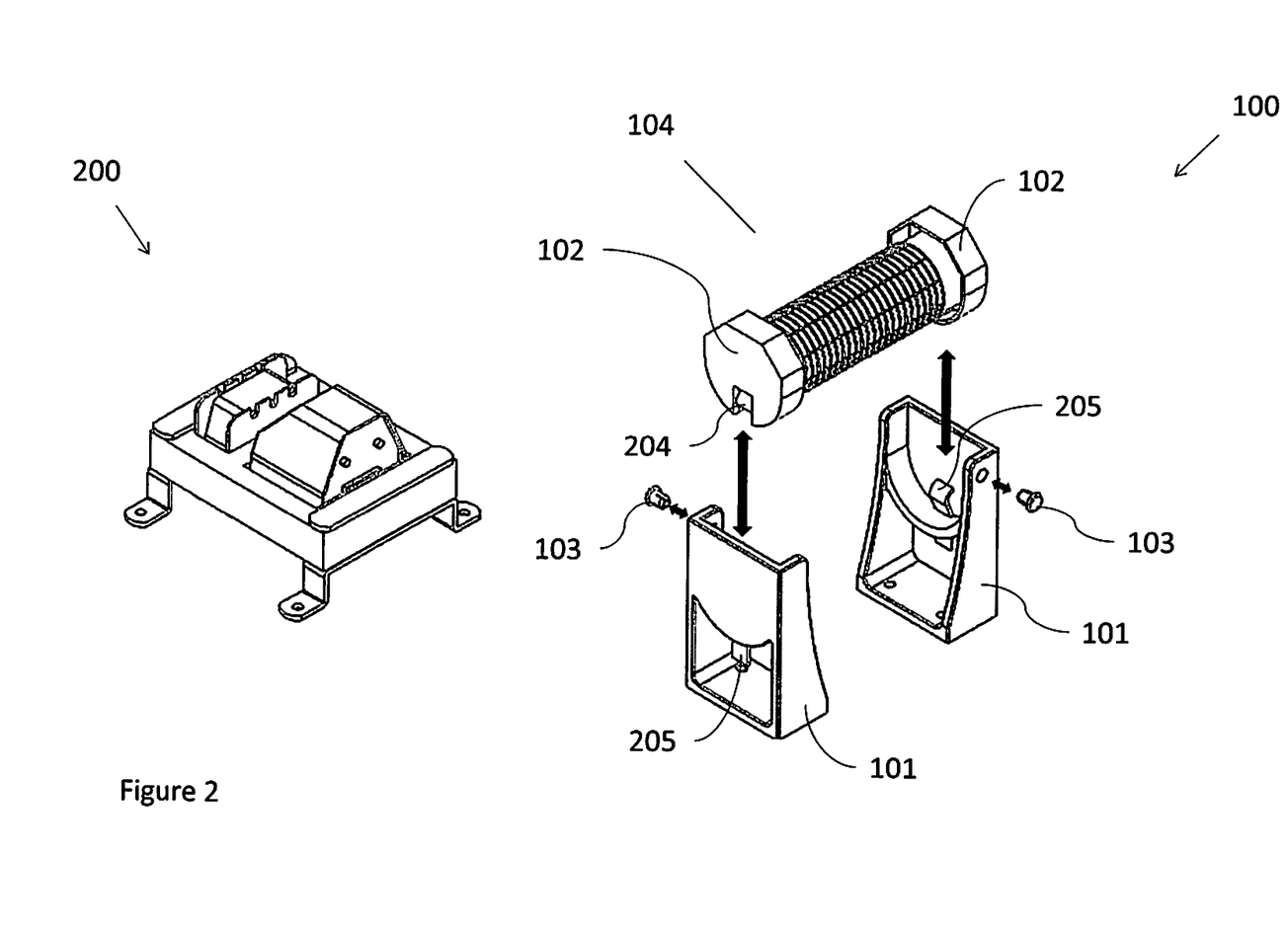
FIG. 2 is an expanded view of the coil assembly of FIG. 1 as well as a high voltage power supply.

As shown with reference to FIG. 2, the coil assembly 100 requires a high voltage power supply 200 to operate. Contacts 205 on the insulated stands 104 are used for applying high voltage to the cylindrical coil 104. As can be appreciated from FIG. 2, the insulated stands 101 act as a set of support holders and the cylindrical coil 104 is detachable from the stands 101. The cylindrical coil 104 is slotted into the insulated stands 101 acting as support holders. It should be appreciated that the cylindrical coil 104 can be easily removed and replaced in the embodiment presented herein. This involves simply retracting the dielectric retainers 103 and lifting the cylindrical coil 104 in the direction of the arrows shown.

It should be appreciated that one of the main advantages of the coil assembly 100 of the present teaching is that cylindrical coil can be easily replaced like changing a battery or a light bulb.

It will be understood by those skilled in the art that power is provided from the power supply 200 to the electrical contacts 205. The exact nature of the connection (e.g., wiring) between the contacts 205 and the power supply can be chosen as appropriate and it is not necessary that the power supply 200 and the coil assembly 100 be collocated. The power from the power supply 200 is then passed through contacts 205 on the insulated stands 101 to the electrical contacts 204 of the cylindrical coil 104. A transformer (not shown) may also be used between the power supply and the contacts 205 to provide high-voltage alternating current.

Figure 3:
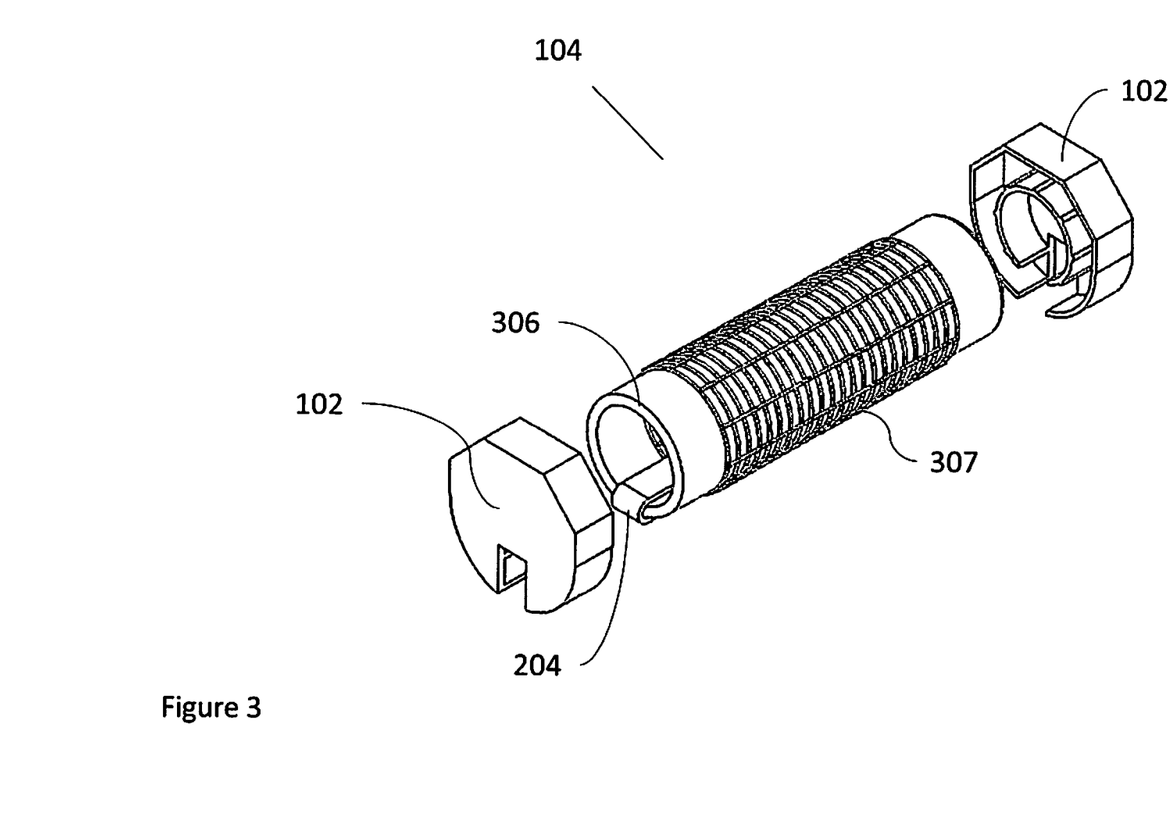
FIG. 3 is a perspective view of the cylindrical coil of figure.

FIG. 3 is a perspective view of the cylindrical coil 104 when removed from the insulating stands 104. It can be seen that the cylindrical coil includes a dielectric insulator tube 306 and an outer electrode 307.

Figure 4:
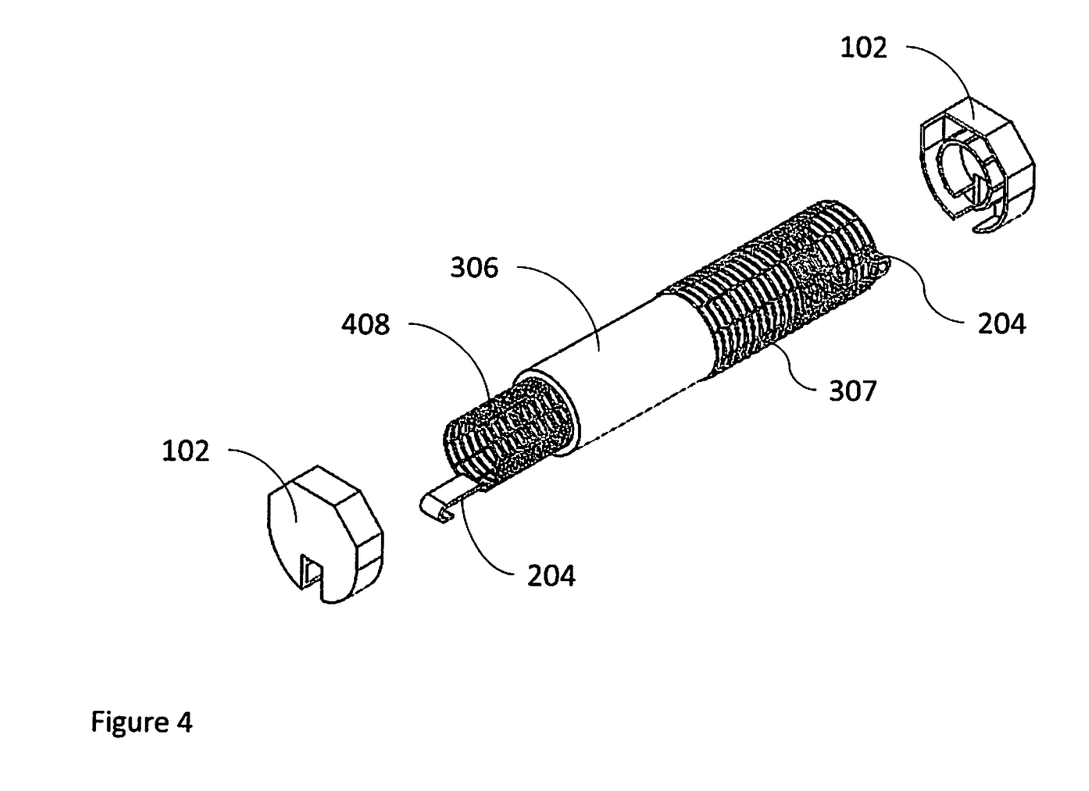
FIG. 4 is an expanded view of the cylindrical coil of FIG. 4.

FIG. 4 is a perspective view of the cylindrical coil of FIG. 3 with the outer electrode 307 offset such that it is only partially overlapping the dielectric 306. In addition, an inner mesh coil acting as an inner electrode 408 is also shown extending from within the insulator tube 306 for ease of viewing. Operably, the inner mesh coil 408 is fully enclosed within the dielectric 306. It can also be appreciated that a first electrical contact 204 is directly attached to the inner electrode 408 such that power is supplied directly to the mesh coil of this electrode 408. The other contact 204 is attached to the outer electrode 307.

The inner and outer wire meshes, which act as inner 408 and outer electrodes 307, maintain direct contact around their respective total surface areas with the dielectric tube 306. This ensures that there are no air pockets around the cylindrical coil where elevated levels of plasma can build up during generation of plasma.

The plasma discharge is generated by applying power to the pair of electrodes i.e., the inner electrode 408 and the outer electrode 307. The applied power sustains either a DC or an AC discharge between, around and/or on the surface of said electrode pair.

Pathogen inactivation and VOC removal is due to interaction of various species and radiation emanating from the plasma discharge with airborne pathogens. Plasma species include, but are not limited to, electrons, ions, and reactive radicals generated by the discharge. In addition the plasma discharge generates electric fields and ultraviolet radiation. The inactivation efficacy of said plasma discharge is proportional to the energy dissipated by the plasma discharge onto a volume of air flowing in the vicinity of the discharge. This energy is proportional to the power applied to sustain the plasma discharge and the exposure time period. The plasma exposure time of a given volume of air flowing through the apparatus is inversely proportional to the air flow.

Thus, it is appreciated that the efficacy of the apparatus described here depends on two basic parameters: the plasma discharge power and the air flow past the electrodes. Those skilled in the art will find that there are a range of power and flow rates that meet various degrees of inactivation while meeting other criteria for the air treatment system, including the number of air changes per hour in a given room size and maximum allowed concentration of radicals generated by the plasma discharge.

The plasma generation in the present teachings is of a dielectric barrier discharge (DBD) type with an inner wire mesh cylinder insulated by a dielectric glass tube. The cylindrical shape of the coil 104 ensures that the outer mesh extends completely circumferentially around the cylindrical coil and that plasma is discharged evenly in all directions from the cylindrical coil.

Dielectric-barrier discharge (DBD) is an electrical discharge between two electrodes separated by an insulating dielectric barrier. Known DBD devices are typically planar, using parallel plates separated by a dielectric or cylindrical, using coaxial plates with a dielectric tube between them. In one coaxial configuration, the dielectric is shaped in the same form as common fluorescent tubing. It is filled at atmospheric pressure with either a rare gas or rare gas-halide mix, with the glass walls acting as the dielectric barrier. Due to the atmospheric pressure level, such processes require high energy levels to sustain. Common dielectric materials include glass, quartz, ceramics and polymers.

It will be appreciated that the voltage and current parameters required to achieve a dielectric barrier discharge will depend principally on the nature of the dielectric used, as further discussed herein below. In general operating voltages below 1 kV are not practical, and preferably there is used an operating voltage in the range from 1 to 6 kV, most desirably from 3 to 5 kV, for example about 4 kV. It will be appreciated that the current required to maintain the dielectric barrier discharge is significantly less than that required to initiate it. The current (and hence power) of plasma generator units is normally expressed in terms of the starting current. There should be used a (starting) current in the range from 1 to 10 mA, preferably at least 3 mA. The power of the unit will of course depend on the voltage and current combination. The power should generally be not more than 50 watts, and is preferably at least 4 watts. Typically the power is in the range from 10 to 40 watts. These power levels have in particular been found to be convenient where the plasma generator is used as part of an apparatus unit having a conduit volume of the order of 0.02 to 1.0 m3.

Even with such low power dielectric barrier discharge units it has been found possible to achieve well contained localized highly inactivating concentrations of anti-pathogenic agents sufficient to inactivate a very wide range of airborne pollutants or pathogens.

Advantageously the plasma generator is coupled to a transformer which is provided with an anti-surge and/or anti-spike device(s), in order to minimize transient excursions of the output voltage above the normal level which could result in temporary extension of the inactivation zone outside of the housing within which the electrodes are provided and/or generation of excessively high anti-pathogenic agent levels.

Importantly, the transformer is located outside of the direct air flow path to minimize the risk of exposure to plasma/anti-pathogenic agents and possible breakdown in the course of use of the apparatus. As previously mentioned, this also ensures that the transformer does not interfere with the flow of air passed the electrode assembly.

An AC supply may also be provided in the apparatus. Preferably, this is co-located with the transformer such that it too does not obstruct airflow. A wide range of frequencies may be used in the AC supply to the low power dielectric barrier discharge device, and indeed somewhat higher frequencies may safely be used than is possible with conventional high power plasma generators. Conveniently an AC supply with a frequency in the range from 50 to 1000 Hz may be used.

It will be appreciated that the sizing and placement of the electrodes that define the discharge unit with respect to the airflow path is quite important. The conduit within which they are located should not be smaller than a volume required to contain the inactivation zone of the plasma generated by the dielectric barrier discharge and not so large that substantially the whole of the airflow within the housing does not pass through said inactivating zone in the course of its transit through apparatus. It will be appreciated that in this context, the inactivating zone is a volume surrounding the discharge unit containing an elevated concentration of anti-pathogenic agents, sufficient to substantially inactivate airborne pollutants or pathogens. The inactivating zone is situated on the outer surface of the discharge unit and in a downstream direction. The total inactivating zone is the combination of all upstream, mid, and downstream stages as anti-pathogenic agents tend to disperse in whole volume and cause deactivation of micro-organisms.

Airflow is desirably passed over and under the electrodes of the discharge unit and not passed through it i.e., there are no air gaps within the discharge unit that allow air to enter or that could potentially hold a build-up in anti-pathogenic agents.

In accordance with the present teaching a discharge unit is provided that is there is desirably used with a solid dielectric to provide a dielectric barrier discharge which the present inventors have found provides in order to obtain a more consistent and reliable plasma generation performance. Various geometries are also possible. However, for the present application, a generally tubular geometry, with a tubular dielectric with generally tubular electrodes on the inner and outer faces thereof is preferred. This tubular shape works to direct the airflow around the discharge unit. It will be appreciated that plasma will be generated at both electrodes. Preferably there is used a generally mesh form electrode, providing a coil, in order to maximize the areas of dielectric surface at which plasma is generated. In this connection it will be appreciated that substantially "closed" meshes are less desirable as these reduce the exposed dielectric surface. On the other hand excessively "open" meshes are generally less efficient in the amount of plasma generated for a give size of unit. Most preferably the electrodes are perfectly coaxial cylindrical mesh where the dielectric is sandwiched between them. In this context preferably the low power discharge unit comprises concentric tubular metal gauze electrodes separated by a dielectric.

In a highly preferred embodiment, the low power discharge plasma unit comprises tubular stainless steel gauze electrodes. Whilst various other suitable electrode materials are known in the art, stainless steel is particularly convenient due to inter alia its resistance to corrosion and to oxidative and other damage from the plasma discharge. The purpose of gauze electrodes is to maximize the surface available for the dielectric barrier corona discharge and hence generation of plasma. However, other factors, such as the effects on the electromagnetic field generated, particularly hysteresis effects relating to the generation and collapse of the field during the 50 Hz cycle of the alternating current, also influence the choice of gauze and the fineness of the mesh. In a preferred embodiment the gauze on the outer electrode is coarser than that of the inner electrode as this favours the production of plasma on the outer, rather than inner, electrode. In a more preferred embodiment, the mesh count of the inner electrode is from 50 to 30*45 to 25 (per inch or 25.4 mm) and that of the outer electrode is 35 to 20*40 to 20. In a particularly favoured embodiment, the mesh count of the inner electrode 204 is 40*34 (per inch or 25.4 mm) using a 38 swg wire (0.15 mm diameter) and that of the outer electrode is 24*28 using a 30 swg wire (0.3 mm diameter).

It is also desirable for effective dielectric barrier discharge to take place that the mass of the electrodes be substantially balanced, i.e. to differ by not more than 20%, preferably not more than 10%. This is especially significant in the case of the aforementioned tubular configuration discharge unit.

It will also be appreciated that the power of the dielectric barrier discharge plasma unit is related to the size of the electrodes. In general it is preferred that each of the mesh electrodes should have an area in the range from 25 to 100 cm2, preferably from 40 to 90 cm2. Typical examples of a coil provided in accordance with the present teaching is one having a length of 5.5 cm or 13 cm and having a diameter of 2.9 cm diameter. Such coils will have exemplary areas of 50 and 118 cm2 respectively. The power consumed by the plasma coils is in the range 10 to 20 W resulting in power density of 0.2 to 0.4 W/cm2 and 0.08 to 0.16 W/cm2 for each coil. Desirably a plasma generator comprising a coil per the present teaching will operate with power density values less than 1 W/cm2 and typically in the range from 0.1 to 0.5 W/cm2.

It will be appreciated that with a solid dielectric, the generation of a plasma through the use of a dielectric barrier discharge is very much dependent on the thickness of the dielectric, and especially at lower voltages, as used in accordance with the present teachings, it is necessary to minimize the thickness of the dielectric. It will also be understood, though, that the discharge unit must be strong enough to avoid damage by the substantial stresses encountered inside a discharge plasma region.

Figure 5:
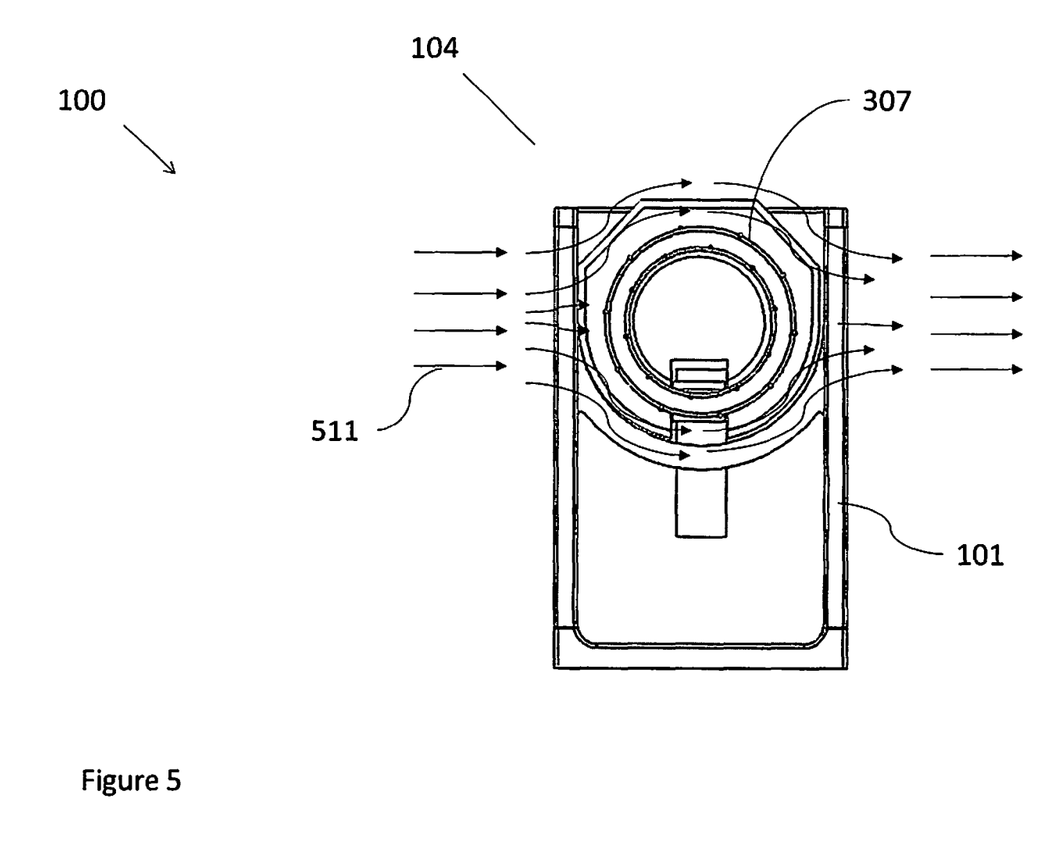
FIG. 5 is a side view of the coil assembly of FIG. 1 as air flows past it.

With reference to FIG. 5, it can be seen that the insulating stands 101 acting as support holders raise or elevate the cylindrical coil 104 above any surface to which the coil assembly 100 may be attached. Such a raised configuration of the coil 104 allows air circulation above and below the coil as shown by the air flow 511. Specifically, by having the electrode assembly raised, an inactivation zone extends completely around the cylindrical coil and air can pass both above and below the cylindrical coil 104 while being subjected to the same level of plasma.

An inactivation zone is a zone in which plasma is released and is effective to inactivate airborne pollutant material entrained in the air flow. Health threatening airborne pollutants may be subdivided into three groups: (a) airborne pathogens comprising any organism that causes disease that spreads throughout the environment via the air; (b) airborne allergens comprising any substance that, when ingested, inhaled, or touched, causes an allergic reaction and, (c) airborne volatile organic compounds (VOC) comprising any product that is designed to be sprayed at high pressure in the form of tiny particles that remain suspended in the air.

The support holders and cylindrical coil 104 are designed and oriented in a manner that air 511 flows in a perpendicular direction and around the outer electrode 307 of the coil through the top and bottom of the cylindrical coil ensuring air exposure to said coil is maximized.

Figure 6:
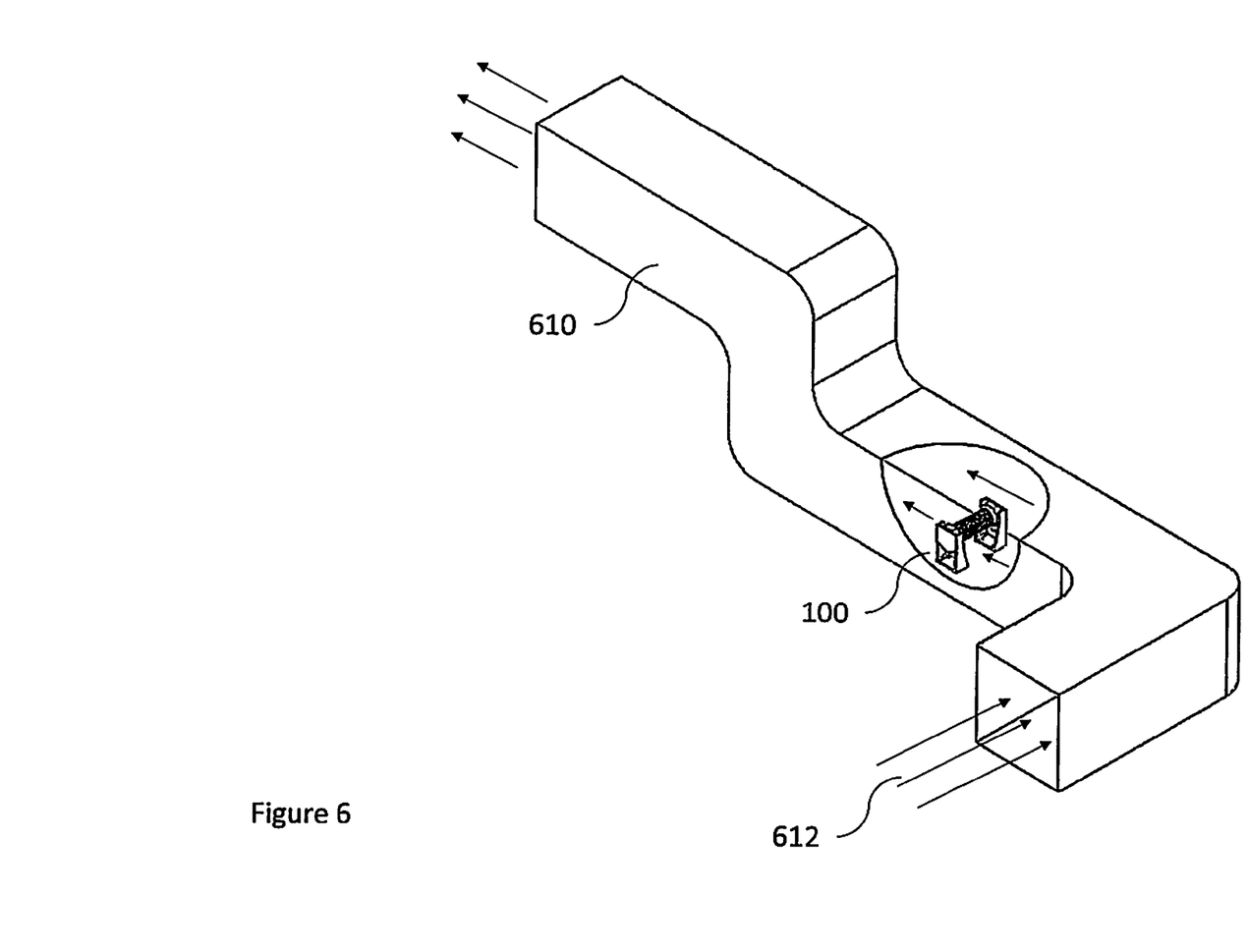
FIG. 6 is a perspective view of the coil assembly of the present teachings within a conduit.

FIG. 6 shows the coil assembly 100 deployed in one possible configuration i.e., within a conduit 610. Air enters the conduit 610 in the direction of arrows 612, flows past the coil assembly 100 and exits at the other end of the conduit. A number of means knows to those skilled in the art could be chosen to induce air flow through the conduit 610, for example an impeller may be used.

The plasma concentration in an inactivating zone, created by the coil assembly 100, is sufficient to effectively inactivate airborne pollutant material entrained in the air flow. Furthermore the concentration of plasma decays sufficiently outside the inactivating zone so that the concentration of any anti-pathogenic agents created by the plasma discharge in the cleaned air expelled from the conduit 610 regions of the apparatus is at a physiologically acceptable level.

Exemplary testing of an apparatus provided in accordance with the present teaching showed efficacy in killing both bacteria and virus. Table 1 shows exemplary data for bacteria testing whereas Table 2 shows similar results for viral testing.

TABLE 1

| Organism | Class | | | | |
|---|---|---|---|---|---|
| *Escherichia coli* | Gram −ve | 2.1E+05 | 0.0E+00 | >5 | >99.999 |
| *S. tyhpi murium* | Gram −ve | 4.6E+05 | 0.0E+00 | >5 | >99.999 |
| *E. agglormerans* | Gram −ve | 3.9E+05 | 0.0E+00 | >5 | >99.999 |
| *E. gergoviae* | Gram −ve | 4.2E+05 | 0.0E+00 | >5 | >99.999 |
| *A. aerogens* | Gram −ve | 7.1E+05 | 0.0E+00 | >5 | >99.999 |
| *S. marcescens* | Gram −ve | 8.2E+05 | 0.0E+00 | >5 | >99.999 |
| *E. sakazakii* | Gram −ve | 3.4E+05 | 0.0E+00 | >5 | >99.999 |
| *Ecoli* O157 H-7 | Gram −ve | 3.5E+05 | 0.0E+00 | >5 | >99.999 |
| *P. aeruginosa* | Gram −ve | 6.1E+05 | 0.0E+00 | >5 | >99.999 |
| *P. putida* | Gram −ve | 8.2E+05 | 0.0E+00 | >5 | >99.999 |
| *S. aureus* oxford | Gram +ve | 4.3E+05 | 0.0E+00 | >5 | >99.999 |
| *S. aureus* MSRA | Gram +ve | 4.8E+05 | 0.0E+00 | >5 | >99.999 |
| *S. epidermidis* | Gram +ve | 3.7E+05 | 0.0E+00 | >5 | >99.999 |
| *M. luteus* | Gram +ve | 9.0E+05 | 0.0E+00 | >5 | >99.999 |
| *S. faecalis* | Gram +ve | 7.3E+05 | 0.0E+00 | >5 | >99.999 |
| *S. pyogenes* | Gram +ve | 3.6E+05 | 0.0E+00 | >5 | >99.999 |
| *B. cereus* | Gram +ve | 7.1E+05 | 0.0E+00 | >5 | >99.999 |
| *B. globigii* | G+ve Spore | 7.9E+05 | 1.0E+01 | >5 | 99.999 |
| *B. subtilis* | G+ve Spore | 2.1E+05 | 3.0E+01 | >5 | 99.986 |
| *B. megaterium* | G+ve Spore | 6.2E+05 | 9.0E+01 | >5 | 99.985 |
| *S. cerevisiea* | Yeast | 4.3E+05 | 0.0E+00 | >5 | >99.999 |
| *S. bailli* | Yeast | 7.2E+05 | 0.0E+00 | >5 | >99.999 |
| *Pichia* mixed eps | Yeast | 6.3E+05 | 0.0E+00 | >5 | >99.999 |
| *S. ludwigii* | Yeast | 6.0E+05 | 0.0E+00 | >5 | >99.999 |
| *A. niger* | Mould mycelial | 6.2E+05 | 0.0E+00 | >5 | >99.986 |
| *A. flavus* | Mould mycelial | 7.8E+05 | 0.0E+00 | >5 | >99.985 |
| *F. poea* | Mould mycelial | 7.2E+05 | 0.0E+00 | >5 | >99.999 |
| *P. digitatum* | Mould mycelial | 6.9E+05 | 0.0E+00 | >5 | >99.999 |
| *F graminerum* | Mould mycelial | 4.3E+05 | 0.0E+00 | >5 | >99.999 |
| *A. niger* | Mould Spore | 8.2E+05 | 7.0E+01 | >5 | 99.991 |
| *A. flavus* | Mould Spore | 6.7E+05 | 5.0E+01 | >5 | 99.993 |
| *F. poea* | Mould Spore | 8.2E+05 | 0.0E+00 | >5 | >99.999 |
| *P. digitatum* | Mould Spore | 6.7E+05 | 0.0E+00 | >5 | >99.999 |
| *F graminerium* | Mould Spore | 2.9E+05 | 0.0E+00 | >5 | >99.999 |

TABLE 2

| Organism | Class | Mean cfu/m$^3$/Hr at input Treatment stream | Mean cfu/m$^3$/Hr post Treatment exit stream | Mean decline Log/cfu/m$^3$/Hr post Treatment exit stream | Apparent percentage reduction |
|---|---|---|---|---|---|
| CTX | SS DNA | 4.3E+12 | 8.1E+02 | >12 | >99.999 |
| ScV-L-BC | DS RNA | 9.2E+12 | 4.6E+02 | >12 | >99.999 |
| FcoV (attenuated) | SS + RNA | 7.1E+12 | 3.0E+02 | >12 | >99.999 |
| T4 Phage | DS DNA | 5.3E+12 | 7.4E+02 | >12 | >99.999 |

In both examples of Table 1 and Table 2, a device per the present teaching with the plasma generator operating at power densities less than 1 W/cm$^2$ achieved>Log 5 kill rate for all classes of bacteria or viral matter.

Situations in which the anti-microbial applications of the invention are especially useful include hospitals, food preparation areas, laboratories and locations with limited ventilation, where air may be re-circulated. Storage of sterile instruments and materials in an atmosphere sterilised by means of the invention may extend their shelf life, with considerable consequent savings. The invention provides a means of supplying a unit for such storage with sterile, dry air capable of maintaining the sterility of stored instruments for extended periods. One particularly useful application is in flood-damaged buildings, where removal of fungal spores from the air can minimize subsequent growth of mould and development of rot in the fabric of the building, with significant reduction in damage and costs of repair. In another application, the apparatus may be installed in ducting or pipework carrying a flow of air, such as may for example be used in an air-conditioning system.

It will be appreciated that in general where airborne pollutants or pathogens are being removed from a room or other more or less enclosed space, the amount of treatment required will depend on the nature of the pollutant/pathogen, and possibly also the burden or loading thereof in the air. Whilst there may in principle be used multiple passes to progressively reduce the pollutant/pathogen loading, it is a particular advantage of the invention that the relatively high anti-pathogenic agent concentrations which can be achieved with apparatus of the invention within the contained inactivation zone, can usually provide substantially complete inactivation within a single pass, thereby minimizing the number of air changes required. Typically where it is desired to remove bacterial pollutants there should be provided at least 5 air changes per hour, whilst in the case of locations with moderate to high tobacco smoke loadings, it may be desirable to provide at least 10 or more air changes. The total airflow required to treat a room may be readily determined from the volume of the room and the number of air changes required.

Whilst it might in principle be possible to achieve higher flow rates with larger sizes of apparatus, it is generally preferred to achieve them by using multiple apparatus units. In this connection it will be appreciated that more than one discharge plasma unit may be mounted in the same conduit, provided the inactivation zones of all the generators are contained within the conduit. Furthermore, more than one discharge unit may be powered by one (common) transformer, albeit the total power of the transformer will then be divided between the discharge units.

It should be noted that various changes and modifications to the presently preferred embodiments described herein will be apparent to those skilled in the art. Such changes and modifications may be made without departing from the spirit and scope of the present invention and without diminishing its attendant advantages. Further, references throughout the specification to "the invention" are nonlimiting, and it should be noted that claim limitations presented herein are not meant to describe the invention as a whole. Moreover, the invention illustratively disclosed herein suitably may be practiced in the absence of any element which is not specifically disclosed herein.

The invention claimed is:

1. A coil assembly for generating plasma comprising:

a cylindrical coil having a first electrode in the form of a cylindrical inner mesh, and having a second electrode in the form of a cylindrical outer mesh;

a cylindrical dielectric separating the inner and outer meshes;

an insulating stand at each of the first and second end of the cylindrical coil configured for mounting the cylindrical coil in an elevated position;

wherein supply of voltage to the inner and outer meshes generates plasma which is discharged from the outer mesh;

wherein the cylindrical dielectric is a solid dielectric such that in use, airflow is passed over and under the electrodes and not passed through the cylindrical dielectric; and wherein the insulating stands act as support holders to elevate the cylindrical coil above any surface to which the coil assembly may be attached, whereby such a raised configuration of the cylindrical coil allows air circulation above and below the cylindrical coil.

2. The coil assembly of claim 1 further comprising electrical contacts on the insulated stands for applying power to the inner and outer meshes.

3. The coil assembly of claim 1 further comprising a retractable retainer on each insulating stand for securing the cylindrical coil to the stands.

4. The coil assembly of claim 1 further comprising insulator caps at each end of the cylindrical coil.

5. The coil assembly of claim 1 further comprising an electrical contact attached to each of the inner and outer meshes.

6. The coil assembly of claim 1 further comprising electrical contacts on the insulated stands for applying power to the inner and outer meshes wherein operably the electrical contacts on the insulating stands make contact with the electrical contact on the inner and outer meshes.

7. The coil assembly of claim 1 configured to operate at a power density less than 1 W/cm$^2$ to operably generate a plasma discharge circumferentially about a longitudinal axis of the cylindrical coil.

8. The coil assembly of claim 7 wherein the operated at a power density in the range from 0.1 to 0.5 W/cm$^2$.

9. The coil assembly of claim 1 comprising concentric tubular metal gauze electrodes separated by a dielectric.

10. The coil assembly of claim 9 wherein the electrodes comprise a mesh.

11. The assembly of claim 10 wherein an inner and outer electrode is provided and the gauze on the outer electrode is coarser than that of the inner electrode to favour production of plasma on the outer, rather than inner, electrode.

12. The assembly of claim 11 wherein the inner electrode has a mesh count of 40*34 per 25.4 mm using a wire of 0.15 mm diameter and the outer electrode has mesh count of 24*28 per 25.4 mm using a wire of diameter 0.3 mm.

13. The assembly of claim 1 configured to limit generation of a discharge to a distance within 1 centimeter of the outer mesh.

14. A conduit comprising the coil assembly of claim 1.

15. The conduit of claim 14 comprising an air flow path, the coil assembly being mounted transverse to the air flow path.

16. The conduit of claim 14 wherein the insulating stand provides the coil in the elevated position to allow air in the air flow path travel under and above the coil.

* * * * *